(12) United States Patent
Li

(10) Patent No.: US 6,878,850 B2
(45) Date of Patent: Apr. 12, 2005

(54) CATALYSIS USING HALOPHOSPHINE COMPOUNDS

(75) Inventor: George Y. Li, Belle Mead, NJ (US)

(73) Assignee: CombiPhos Catalysts, Inc, Princeton, NJ (US)

( * ) Notice: Subject to any disclaimer, the term of this patent is extended or adjusted under 35 U.S.C. 154(b) by 0 days.

(21) Appl. No.: 10/353,501

(22) Filed: Jan. 29, 2003

(65) Prior Publication Data

US 2004/0147392 A1 Jul. 29, 2004

(51) Int. Cl.$^7$ .............................................. C07C 41/00
(52) U.S. Cl. ....................................................... 568/10
(58) Field of Search ........................................... 568/10

(56) References Cited

U.S. PATENT DOCUMENTS

| | | |
|---|---|---|
| 5,756,804 A | 5/1998 | Haber et al. |
| 5,801,263 A | 9/1998 | Seitz et al. |
| 6,124,462 A | 9/2000 | Li |
| 6,291,722 B1 | 9/2001 | Li |

OTHER PUBLICATIONS

John F. Hartwig, Palladium–Catalyzed Amination of Aryl Halides: Mechanism and Rational Catalyst Design, Apr. 18, 1996, p. 329–340, Synlett.

Akira Suzuki, Recent advances in the cross–coupling reactions of organoboron derivatives with organic electrophiles, 1995–1998, p. 147–168, Journal of Organometallic Chemistry 576 (1999).

Genet, et al., Recent developments of palladium(0) catalyzed reactions in aqueous medium, 1999, p. 305–317, Journal of Organometallic Chemistry 576.

Wolfe, et al., A Highly Active Catalyst for the Room–Temperature Amination and Suzuki Coupling of Aryl Chlorides, 1999, p. 2413–2416, Angew. Chem. Int. Ed. 1999,38, No. 16.

Hartwig, et al., Room–Temperature Palladium–Catalyzed Amination of Aryl Bromides and Chlorides and Extended Scope of Aromatic C –N Bond Formation with a Commercial Ligand, 1999, p. 5575–5580, J. Org. Chem., 1999, 64.

Littke, et al., Palladium–Catalyzed Coupling Reactions of Aryl Chlorides, 2002, p. 4177–4211, Agnew. Chem. Int. Ed., 2002, 41.

*Primary Examiner*—Zinna Northington Davis
(74) *Attorney, Agent, or Firm*—Mathews, Collins, Shepherd & McKay, P.A.

(57) ABSTRACT

The present invention provides the preparation and use of halophosphine-transition metal complex as catalysts for cross-coupling reaction to produce substituted aromatic heterocycles, biaryls and arylamines by reacting pyridyl halides or aryl halides with arylboronic acids or amines.

4 Claims, No Drawings

CATALYSIS USING HALOPHOSPHINE COMPOUNDS

FIELD OF INVENTION

The invention relates to the use of halophosphine compounds complexed with transition metals to produce substituted aromatic heterocycles, biaryls and arylamines via cross-coupling reactions with aryl halides and arylboronic acids or amines.

BACKGROUND OF THE INVENTION

Chelating phosphine compounds when bound to metal atoms are generally known to be useful as catalysts. One reaction which uses palladium phosphine catalysts is the coupling of aryl halides with amines for the production of arylamines, as reviewed by Hartwig, SYNLETT, 1997, (4), PG. 329–340. An example of this reaction is the coupling of 4-bromotoluene and diphenylamine to form tolyldiphenylamine:

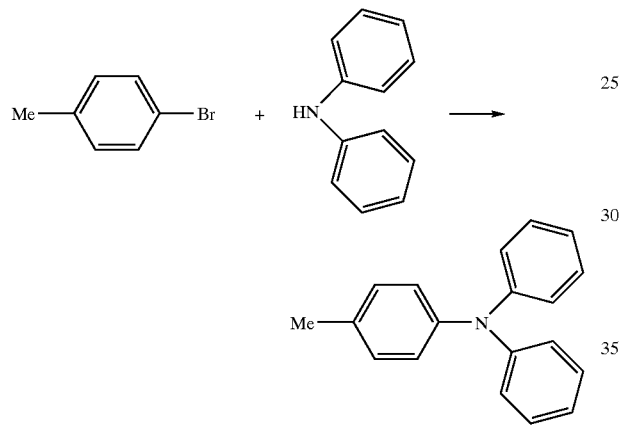

Another reaction is which palldium/phosphine catalysts have been used is the Suzuki reaction, where biaryls are produced through the coupling of arylboronic acids and aryl halides, as reviewed by Suzuki, A, J. Orgmet. Chem., 576 (1999), pg. 147. One example of this reaction is the preparation of 2-phenylpyridine from phenylboronic acid and 2-chloropyridine:

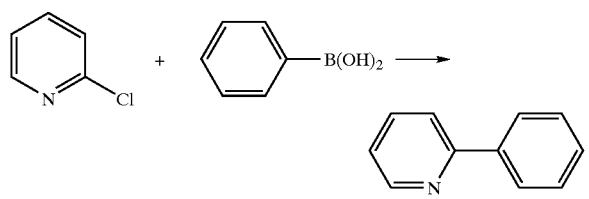

Both of theses products are important classes of compounds used in the manufacture of pharmaceuticals, agrochemicals, advanced materials, polymers and ligands, and much work has been done on their preparation. However, there is an expanding need for stable, easily prepared catalysts that result in good yields and mild reaction conditions.

BRIEF SUMMARY OF THE INVENTION

One aspect of the invention is to develop halophosphine-transitional metal compounds having the general formula (I)

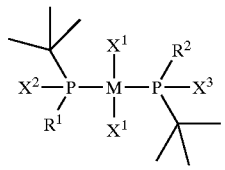

wherein M is a transition metal;

$X^1$ is Cl or Br or I; $X^2$ is Cl or Br or I; $X^3$ is Cl or Br or I;

$R^1$ and $R^2$ are independently selected from the group consisting of hydrocarbyl, substituted hydrocarbyl, heterocyclic, organometallic, H, CN, Cl, Br, I, CN, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic, and optionally $R^1$ and $R^2$ can together form a ring. Preferably, $R^1$ and $R^2$ are $C_1$–$C_{10}$ alkyl.

More preferably, $R^1$ and $R^2$ are tert-butyl. Even more preferably $R^1$ and $R^2$ are tert-butyl and M is a Pd.

Another aspect of the invention is to develop a process to prepare cross-coupling compounds of the formula $R^1$—Q in the presence of a catalytic amount of a coordination compounds of formula (I), or formula (II).

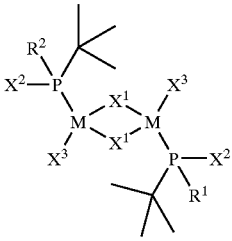

In formula (II), wherein M is a transition metal; $X^1$ is Cl or Br or I; and $X^2$ is Cl or Br or I; $X^3$ is Cl or Br or I; $R^1$ and $R^2$ are independently selected from the group consisting of hydrocarbyl, substituted hydrocarbyl, heterocyclic, organometallic, H, CN, Cl, Br, I, CN, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic, and optionally $R^1$ and $R^2$ can together form a ring.

In $R^1$—Q, $R^1$ is an optionally selected from aryl; Q is independently selected from the group consisting of hydrocarbyl, substituted hydrocarbyl, heterocyclic, organometallic, CN, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic.

Another aspect of the invention is to develop a method to prepare arylamines of the formula $R^1$—$NR^2R^3$ comprising contacting an amine of the formula $HNR^2R^3$ with an aryl compound of the formula $R^1$—X in the presence of a catalytic amount of coordination compound comprising one or more transition metals complexed to a halophosphine ligand of the formula $XPR^4R^5$; wherein X is a halogen; $R^1$ is an optionally substituted aromatic heterocyclic, aryl; $R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring; and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$, are independently selected from the group consisting of hydrogen, hydrocarbyl substituted hydrocarbyl, hydrocarbylamino, alkoxy, aryloxy, and heterocyclic. Optionally $R^4$ and $R^5$ can together form a ring.

Preferably, $R^1$ is an optionally substituted aromatic heterocyclic or aryl, and the transition metal is selected from Periodic Group VIII. More preferably, $R^4$ and $R^5$ are independently selected from the group consisting of hydrocarbyl, substituted hydrocarbyl and heterocyclic, the transition metal is Pd or Ni, and $R^2$ and $R^3$ are selected from the group consisting of hydrogen, optionally substituted aryl, and wherein $R^2$ and $R^3$ are hydrocarbyl and together from a ring. Most preferably X is Cl, or Br or I, $R^1$ is selected from the group consisting of phenyl, pyridyl; $R^2$ and $R^3$ are selected from the group consisting of hydrogen, phenyl, and pyridyl; and $R^4$ and $R^5$ are selected from the group consisting of t-butyl or ferrocenyl.

Another aspect of the invention is directed to a process to prepare substituted heterocycles of the formula $R^1$–$R^6$ comprising contacting a boronic acid of the formula $R^6$—B(OH)$_2$, or a boronic acid ester of the formula $R^6$—$B(OR^7)_2$ with an aromatic heterocyclic compound of the formula $R^1$—X or an aryl compound of the formula $R^1$—X in the presence of a catalytic amount of a coordination compound comprising one or more transition metals complexed to a halophosphine ligand of the formula $XPR^4R^5$ wherein X is a halogen; $R^1$ is an optionally substituted pyridyl or aryl; $R^6$ is selected from the group consisting of hydrocarbyl, substituted hydrocarbyl, hydrocarbyl amino, alkoxy, aryloxy, and heterocyclic; $R^7$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$, are independently selected from the group consisting of hydrogen, hydrocarbyl substituted hydrocarbyl, hydrocarbylamino, alkoxy, aryloxy, and heterocyclic. Optionally $R^4$ and $R^5$ can together form a ring.

Preferably $R^1$ is an optionally substituted pyridyl, and the transition metal is selected from Periodic Group VIII. More preferably $R^4$ and $R^5$ are independently selected from the group consisting of hydrocarbyl, substituted hydrocarbyl and heterocyclic, the transition metal is Pd or Ni, and $R^6$ is an optionally substituted aryl. Most preferably X is Cl or Br or I, $R^1$ is selected from the group consisting of phenyl or aromatic heterocyclic; and $R^4$ and $R^5$ are selected from the group consisting of t-butyl or ferrocenyl.

Another aspect of the invention is directed to a process to prepare substituted aromatic heterocycles or biaryls of the formula $R^1$—S—$R^8$ or $R^1$—O—$R^9$ comprising contacting a thioether of the formula of $R^8SH$, or an alcohol of the formula of $R^9OH$, with an aromatic heterocyclic compound of the formula $R^1$—X or an aryl compound of the formula $R^1$—X in the presence of a catalytic amount of a coordination compound comprising one or more transition metals complexed to a halophosphine ligand of the formula $XPR^4R^5$ wherein X is a halogen; $R^1$ is an optionally substituted pyridyl or aryl; $R^8$ or $R^9$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic, Optionally $R^4$ and $R^5$ can together form a ring.

Preferably $R^1$ is an optionally substituted pyridyl or aryl, and the transition metal is selected from Periodic Group VIII. More preferably $R^4$ and $R^5$ are independently selected from the group consisting of hydrocarbyl, substituted hydrocarbyl and heterocyclic, and optionally $R^4$ and $R^5$ can together form a ring. The transition metal is Pd, and $R^6$ is an optionally substituted aryl. Most preferably X is Cl, or Br or I, $R^1$ is selected from the group consisting of phenyl or aromatic heterocyclic; and $R^4$ and $R^5$ are selected from the group consisting of t-butyl or ferrocenyl.

Another aspect of the invention is directed to a process to prepare substituted aromatic heterocycles or biaryls of the formula $R^1$–$R^9$ comprising contacting an organometallic compound of the formula of $R^{10}M$, wherein M is a MgX, or a ZnX, or a $ZnR^{11}$, or a Li, or a Na, or a K, with an aromatic heterocyclic compound of the formula $R^1$—X or an aryl compound of the formula $R^1$—X in the presence of a catalytic amount of a coordination compound comprising one or more transition metals complexed to a halophosphine ligand of the formula $XPR^4R^5$ wherein X is a halogen; $R^1$ is an optionally substituted pyridyl or aryl; $R^{10}$ is selected from the group consisting of hydrocarbyl, substituted hydrocarbyl, hydrocarbylamino, alkoxy, aryloxy, and heterocyclic; $R^{11}$ is selected from the group consisting of CN, hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic. Optionally $R^4$ and $R^5$ can together form a ring.

Preferably $R^1$ is an optionally substituted pyridyl, and the transition metal is selected from Periodic Group VIII. More preferably $R^4$ and $R^5$ are independently selected from the group consisting of t-butyl, the transition metal is Pd or Ni, and $R^6$ is an optionally substituted aryl. Most preferably X is Cl, or Br or I, $R^1$ is selected from the group consisting of phenyl or aromatic heterocyclic.

A further aspect of the invention includes the method of using halophosphines as ligands for homogeneous catalysis of arylamines of the formula $R^1$—$NR^2R^3$ or biaryls of the formula $R^1$–$R^6$ comprising (1) preparing a coordination compound comprising one or more transition metals complexed to a halophosphine compound of the formula $XPR^4R^5$, wherein X is a halogen; $R^1$ is an optionally substituted aromatic heterocyclic or aryl; $R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, CN, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic, optionally $R^4$ and $R^5$ can together form a ring, and (2) contacting (i) a boronic acid of the formula $R^6$—$B(OH)_2$, (ii) a boronic acid ester of the formula $R^6$—B$(OR^7)_2$ or (iii) an amine of the formula $HNR^2R^3$ with an aryl compound of the formula $R^1$—X in the presence of a catalytic amount of the coordination compound prepared in step (1) to form, respectively, arylamines of the formula $R^1$—$NR^2R^3$ or aromatic heterocycles of the formula $R^1$-$R^6$ Various patents and publications are cited throughout the present application. The contents of these patents and publications cited herein and the contents of documents cited in these patents and publications are hereby incorporated herein by reference to the extent permitted.

REFERENCES

1. Haber, U.S. Pat. No. 5,756,804;
2. Seitz, U.S. Pat. No. 5,801,263;
3. Li, U.S. Pat. No. 6,124,462;
4. Li, U.S. Pat. No. 6,291,722 B1;
5. Hartwig, John F., Palladium-Catalyzed Amination of Aryl Halides: Mechanism and Rational Catalyst Design, *Synlett*, 4, 329–340, 1997;
6. Suzuki, Akira, Recent Advances in the Cross-Coupling Reactions of Organoboron Derivatives with Organic Electrophiles, 1995–1998, *Journal of Organometallic Chemistry*, 576, 147–168, 1999;
7. Genet, Jean P. et al., Recent Development of Palladium(0) Catalyzed Reactions in Aqueous Medium, *Journal of Organometallic Chemistry*, 576, 305–317, 1999;
8. Wolfe, John P., et al., A highly Active Catalyst for the Room-Temperature Amination and Suzuki Coupling of Aryl Chlorides, *Angewandte Chemie International Edition*, 1999, 2413–2416, 38, No. 16, Wiley-VCH Verlag GmbH, Weinheim, Germany;
9. Hartwig, John F., et al., Room-Temperature Palladium-Catalyzed Amination of Aryl Bromides and Chlorides and Extended Scope of Aromatic C—N Bond Formation with a Commercial Ligand, *Journal of Organic Chemistry*, 1999, 5575–5580, 64, American Chemical Society, Easton, USA; and
10. Littke, Adam F., et al., Palladium-Catalyzed Coupling Reactions of Aryl Chlorides, *Angewandte Chemie International Edition*, 2002, 4176–4211, 41, Wiley-VCH Verlag GmbH, Weinheim, Germany.

DETAILED DESCRIPTION OF THE INVENTION

This disclosure sets out methods for the use of halophosphine compounds complexed with transition metals to produce substituted aromatic heterocycles, biaryls and arylamines via cross-coupling reactions with heterocyclic halides, aryl halides and arylboronic acids or arylboronic ester or amines. Halophosphines were not previously used as ligands in homogeneous catalysis, primarily because the extreme unstability of halophosphines; X-atoms in $XPR^4R^5$ are easily replaced by nucleophilic groups.

Without intending to be bound by any particular theory of operation, it is believed that the substituted heterocycles, biaryls and arylamines were produced via cross-coupling reactions between aryl halides and arylboronic acids or amines in the presence of a catalyst, such as halophosphine compounds complexed with transition metals. The processes of the instant invention are an improvement over similar processes in the art. The highly unstable halophosphines used in the instant processes are easily stabilized by complexing with transition metals, the formed ligand-metal complexes are air- and moisture-stable solids and are easily handled, and can be easily synthesized in a variety of ratios of Metals/halophosphines. The processes are easily adapted to a variety of C—C, C—N, C—S, C—O, C—B, and C—P bond formations via cross-coupling reactions and can be used to construct libraries of aromatic heterocycles, biaryls and arylamines, which are widely used in the manufacture of pharmaceuticals, agrochemicals, advanced materials, liquid polymers and ligands.

Generally, arylamines of the formula $R^1$—$NR^2R^3$ can be prepared by reacting amines with aryl halides. A preferred process of preparing arylamines of the formula $R^1$—$NR^2R^3$ includes contacting an amine of the formula $HNR^2R^3$ with an aryl compound of the formula $R^1$—X in the presence of a catalytic amount of a coordination compound comprising one or more transition metals complexed to a halophosphine compound of the formula $XPR^4R^5$. In this process, X is a halogen; $R^1$ is an optionally substituted aryl radical, $R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring, and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, and $NQ_5Q_6$, where $Q_1$, $Q_2$, $Q_3$, $Q_4$, $Q_5$, $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring. Optionally, the process can be performed intramolecularly; i.e. the amine functionality and the aryl functionality are both located on the same compound and the process results in a cyclization.

The halophosphine compound can be prepared by any method, including any of the well-known processes in the art and combinatorial methods using polymer supports in PCT Int. Appl. (2000), WO 00/21663. The amine and the aryl compound can be prepared by any method, including any of the well-known processes in the art.

As used herein, the phrase "coordination compound" refers to a compound formed by the union of a metal ion (usually a transition metal) with a non-metallic ion or molecule called a ligand or complex-forming agent.

"Transition metals" include metals having atomic weight 21 through 83. Preferably, the transition metal is from Periodic Group VIII (defined as Fe, Co, Ni, Ru, Rh, Pd, Os, Ir, and Pt). More preferred are Pd and Ni. The complex can be made by any synthetic method known in the art, either through direct reaction or via the use of a halophosphine precursor or a transition metal precursor.

The halophosphine compound used in the instant invention can exist in X—$PR^4R^5$ form when presents as a component of the complex. The complex can be isolated and purified before use, or be prepared and used in situ. Many of these techniques are described in Hartly, F. R. (Ed), "Chem. Met.-Carbon Bond", 1987, vol. 4, pp. 1163–1225) and the content of which is incorporated herein by reference to the extent permitted.

The phrase "hydrocarbyl" means a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Nonlimiting examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methyl-cyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include methoxy, phenoxy, toluyl, chlorobenzyl, fluoroethyl, p-Me—S—C6H5,2-methoxypropyl.

The phrase "aryl" means an aromatic carbocyclic group having a single ring (e.g., phenyl, pyridyl), multiple rings (e.g., biphenyl), or multiple condensed rings in which at least one is aromatic (e.g., napthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. By aryl is also meant heteroaryl groups where heteroaryl is defined as 5-, 6-, or 7-membered aromatic ring systems having at least one hetero atom selected from the group consisting of nitrogen, oxygen and sulfur. Nonlimiting examples of heteroaryl groups are pyridyl, pyrimidinyl, pyrrolyl, pyrazolyl, pyrazinyl, pyridazinyl, oxazolyl, which can optionally be substituted with, e.g., halogen, lower alkyl, lower alkoxy, lower alkylthio, trifluoromethyl, lower acyloxy, aryl, heteroaryll, and hydroxy.

The phrase "ring" means a linking group having a single ring (e.g., phenyl, pyridyl), multiple rings (e.g., biphenyl, ferrocenyl), or multiple condensed rings in which at least one is aromatic (e.g., naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. By ring is also meant optionally-substituted chains of from 1 to 12 linear, branched, and cyclic carbon atoms.

A preferred process is where $R^1$ is an optionally substituted aromatic heterocycle, $R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring, and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic, and optionally $R^4$ and $R^5$ can together form a ring. More preferred is where X is Cl. Also preferably, the transition metal is from Periodic Group VIII. More preferred is Pd. Reactions of Arylboronic Acids with Aromatic Heterocyclic Halides to Prepare Substituted Aromatic Heterocycles of the Formula $R^1$–$R^6$.

The instant invention also describes a process to prepare substituted aromatic heterocycles, biaryls of the formula $R^1$–$R^6$ comprising contacting a boronic acid of the formula $R^6$—B(OH)$_2$ or arylboronic acid ester of the formula $R^6$—B(OR$^7$)$_2$ with an aryl compound of the formula $R^1$—X in the the presence of a catalytic amount of a coordination compound comprising one or more transition metals complexed to a halophosphine compound of the formula X—PR$^4$R$^5$; where X is a halogen, $R^1$ and $R^6$ and $R^7$ are selected from the group consisting of hydrocarbyl, substituted hydrocarbyl, hydrocarbylamino, alkoxy, aryloxy, and heterocyclic, and $R^4$ and $R^5$ are independently selected from the group consisting of hydrocarbyl, substituted hydrocarbyl, heterocyclic, organometallic, H, CN, Cl, Br, I, $SQ_1$, $OQ_2$, $PQ_3Q_4$, $NQ_5Q_6$, $SiQ_7Q_8Q_9$, and $BQ_{10}Q_{11}$ where $Q_1$, $Q_2$, $Q_3$, $Q_4$, $Q_5$, $Q_6$, $Q_7$, $Q_8$, $Q_9$, $Q_{10}$, and $Q_{11}$ are independently selected from the group consisting of hydrogen, hydrocarbyl substituted hydrocarbyl, hydrocarbylamino, alkoxy, aryloxy, and heterocyclic. Optionally $R^4$ and $R^5$ can together form a ring. Optionally, the process can be performed intramolecularly; i.e., the boronic acid or boronic ester functionality and aryl functionality are both located on the same compound and the process results in a cyclization.

A preferred process is where $R^1$ is an optionally substituted aromatic heterocycle, $R^4$ and $R^5$ are independently selected from the group consisting of hydrocarbyl, substituted hydrocarbyl, heterocyclic, organometallic, CN, $SQ_1$, $OQ_2$, $PQ_3Q_4$, $NQ_5Q_6$, $SiQ_7Q_8Q_9$, and $BQ_{10}Q$, 1 where $Q_1$, $Q_2$, $Q_3$, $Q_4$, $Q_5$, $Q_6$, $Q_7$, $Q_8$, $Q_9$, $Q_{10}$, and $Q_{11}$, are independently selected from the group consisting of hydrogen, hydrocarbyl substituted hydrocarbyl, hydrocarbylamino, alkoxy, aryloxy, and heterocyclic. Optionally $R^4$ and $R^5$ can together form a ring. $R^6$ is selected from the group consisting of aryl, aromatic heterocyclic. $R^7$ is selected from the group consisting of methyl, ethyl, iso-propyl, phenyl, ethylenyl. More preferred is where X is Cl or Br. Also preferably, the transition metal is from Periodic Group VIII. More preferred is Pd or Ni.

The following non-limiting Examples are meant to illustrate the invention but are not intended to limit it in any way.

EXAMPLES

All manipulations of air-sensitive materials were carried out with rigorous exclusion of oxygen and moisture in flame-dried Schlenk-type glassware on a dual manifold Schlenk line, interfaced to a high-vacuum ($10^{-4-10-5}$ Torr) line, or in a nitrogen-filled Vacuum Atmospheres glovebox with a high-capacity recirculator (1–2 ppm of $O_2$). Before use, all solvents were distilled under dry nitrogen over appropriate drying agents (sodium benzophenone ketyl, metal hydrides except for chlorinated solvents). Deuterium oxide and chloroform-d were purchased from Cambridge Isotopes. All organic and inorganic starting materials were purchased from Aldrich Chemical Co. (Milwaukee Wis.), Strem Chemicals (Newburyport, Mass.), or Lancaster Synthesis Inc. (Windham, N.H.), and when appropriate were distilled prior to use.

NMR spectra were recorded on either a Nicolet NMC-300 wide-bore (FT, 300 MHz, $^1$H; 75 MHz, $^{13}$C, 121 MHz, $^{31}$P), or GE QM-300 narrow-bore (FT, 500 MHz, $^1$H) instrument. Chemical shifts ($\delta$) for $^1$H, $^{13}$C are referenced to internal solvent resonances and reported relative to SiMe$_4$. $^{31}$P NMR shifts are reported relative to external phosphoric acid.

Example 1

Synthesis of (t-Bu)$_2$PCl)$_2$PdCl$_2$ Isomers
[Formula (I)]

In the drybox, 236 g (1.306 moles) of (Me$_3$C)$_2$P—Cl, 100 g (0.564 moles) of PdCl$_2$ and 600 mL of THF were loaded into a reactor (2000 mL) equipped with a magnetic stir bar. The resulting mixture was stirred at room temperature overnight before refluxing for 3 hours. The reaction solution was cooled to room temperature, and 2000 mL of THF was added to dissolve most of solids. After passing through a SiO$_2$ gel column in the drybox to remove some by-products, the eluate was dried under vacuum, and the resulting solids were washed with H$_2$O (4×250 mL), hexane (2×200 mL), recrystallized from THF and hexane, and dried under vacuum overnight to afford two isomers of (t-Bu)$_2$PCl)$_2$ PdCl$_2$ (288 g, 94% yield). $^1$H NMR (500 MHz, CDCl$_3$): $\delta$ 1.57 (d, J=8.0 Hz), 1.55 (d, J=8.8 Hz) ppm. $^{13}$C NMR (125 MHz, CDCl$_3$): $\delta$ 43.9, 30.0 ppm. $^{31}$P NMR (121 MHz, CDCl$_3$): $\delta$ 150.7, 143.2 ppm.

Example 2

Synthesis of [(t-Bu)$_2$P(Cl)PdCl$_2$]$_2$ [Formula (II)]

In the drybox, 42 g (0.232 moles) of (Me$_3$C)$_2$P—Cl, 40 g (0.226 moles) of PdCl$_2$ and 250 mL of CH$_2$Cl$_2$ were loaded into a reactor (1000 mL) equipped with a magnetic stir bar. The resulting mixture was stirred at room temperature for 5 hours before refluxing for 1 hour. After cooling to room temperature, 2000 mL of CH$_2$Cl$_2$ was added to dissolve most of solids, the resulting mixture was passed through a SiO$_2$ gel column to remove some by-products. The eluate was dried under vacuum, the resulting solid was washed with H$_2$O (4×100 mL), hexane (2×200 mL), and recrystallized from CH$_2$Cl$_2$ and THF. The resulting solid was dried under vacuum to afford [(t-Bu)$_2$P(Cl)PdCl$_2$]$_2$ (136 g, 84% yield). $^1$H NMR (500 MHz, CDCl$_3$): δ 1.61 (d, (d, J=18.0 Hz) ppm. $^{13}$C NMR (125 MHz, CDCl$_3$): δ 46.1, 29.6 ppm. $^{31}$P NMR (121 MHz, CDCl$_3$): δ 163.4 ppm.

Example 3

Reactions of Amines with Aryl Halides

A 30 mL of reactor equipped with magnetic stir bar was charged with 70 mg (0.13 mmol) of (t-Bu)$_2$PCl)$_2$PdCl$_2$, 0.88 g (5.14 mmol) of 4-bromotoluene, 0.70 g (4.14 mmol) of Ph$_2$NH and 0.48 g (8.55 mmol) of KOH in 2 mL of toluene. The reaction mixture was refluxed for 5 hours. The reaction mixture was cooled to room temperature, transferred to a separatory funnel, and diluted with 100 mL of diethyl ether and 20 mL of H$_2$O. The layers were separated, and organic layer was washed with H$_2$O (2×50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give p-tolyldiphenylamine. LC-MS Found: 260.3 (M$^+$+1).

Example 4

A 30 mL of reactor equipped with magnetic stir bar was charged with 50 mg (0.09 mmol) of (t-Bu)$_2$PCl)$_2$PdCl$_2$, 0.50 g (4.4 mmol) of 2-chloropyridine, 0.70 g (4.14 mmol) of Ph$_2$NH and 0.58 g (5.17 mmol) of KO-t-Bu in 2 mL of toluene. The reaction mixture was refluxed overnight. The reaction mixture was cooled to room temperature, transferred to a separatory funnel, and diluted with 100 mL of diethyl ether and 20 mL of H$_2$O. The layers were separated, and organic layer was washed with H$_2$O (2×50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give 2-pyridyldiphenylamine. LC-MS Found: 247.3 (M$^+$+1).

Example 5

A 30 mL of reactor equipped with magnetic stir bar was charged with 33 mg (0.046 mmol) of [(t-Bu)$_2$P(Cl)PdCl$_2$]$_2$, 0.50 g (4.4 mmol) of 2-chloropyridine, 0.70 g (4.14 mmol) of Ph$_2$NH and 0.58 g (5.17 mmol) of KO-t-Bu in 2 mL of toluene. The reaction mixture was refluxed overnight. The reaction mixture was cooled to room temperature, transferred to a separatory funnel, and diluted with 100 mL of diethyl ether and 20 mL of H$_2$O. The layers were separated, and organic layer was washed with H$_2$O (2×50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give 2-pyridyldiphenylamine. LC-MS Found: 247.3 (M$^+$+1).

Example 6

A 30 mL of reactor equipped with magnetic stir bar was charged with 50 mg (0.093 mmol) of (t-Bu)$_2$PCl)$_2$PdCl$_2$, 0.50 g (4.4 mmol) of 3-bromopyridine, 0.50 g (3.16 mmol) of Ph$_2$NH and 0.25 g (4.46 mmol) of KOH in 2 mL of 1,4-dioxane. The reaction mixture was refluxed for 5 hours. The reaction mixture was cooled to room temperature, transferred to a separatory funnel, and diluted with 100 mL of diethyl ether and 20 mL of H$_2$O. The layers were separated, and organic layer was washed with H$_2$O (2×50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give 3-pyridyldiphenylamine. LC-MS Found: 247.3 (M$^+$+1).

Example 7

Reactions of Arylboronic Acids with Aryl Halides

A 30 mL of reactor equipped with magnetic stir bar was charged with 54 mg (0.10 mmol) of (t-Bu)$_2$PCl)$_2$PdCl$_2$, 0.50 g (4.4 mmol) of 2-chloropyridine, 0.65 g (5.33 mmol) of PhB(OH)$_2$ and 0.40 g (7.13 mmol) of KOH in 2 mL of 1,4-dioxane. The reaction mixture was refluxed for 7 hours. The reaction mixture was cooled to room temperature, transferred to a separatory funnel, and diluted with 100 mL of diethyl ether and 20 mL of H$_2$O. The layers were separated, and organic layer was washed with H$_2$O (50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give 2-phenylpyridine. LC-MS Found: 156.2 (M$^+$+1).

Example 8

A 30 mL of reactor equipped with magnetic stir bar was charged with 23.7 mg (0.044 mmol) of (t-Bu)$_2$PCl)$_2$PdCl$_2$, 0.50 g (4.4 mmol) of 2-chloropyridine, 0.65 g (5.33 mmol) of PhB(OH)$_2$ and 0.92 g (6.67 mmol) of K$_2$CO$_3$ in 3 mL of EtOH (95%). The reaction mixture was refluxed for 5 hours. The reaction mixture was cooled to room temperature, transferred to a separatory funnel, and diluted with 100 mL of diethyl ether and 20 mL of H$_2$O. The layers were separated, and organic layer was washed with H$_2$O (50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give 2-phenylpyridine. LC-MS Found: 156.2 (M$^+$+1).

Example 9

A 30 mL of reactor equipped with magnetic stir bar was charged with 15.8 mg (0.022 mmol) of [(t-Bu)$_2$P(Cl)PdC$_2$]$_2$, 0.50 g (4.4 mmol) of 2-chloropyridine, 0.65 g (5.33 mmol) of PhB(OH)$_2$ and 0.92 g (6.67 mmol) of K$_2$CO$_3$ in 3 mL of EtOH. The reaction mixture was refluxed for 5 hours. The reaction mixture was cooled to room temperature, transferred to a separatory funnel, and diluted with 100 mL of diethyl ether and 20 mL of H$_2$O. The layers were separated, and organic layer was washed with H$_2$O (50 mL), brine (30 mL), and dried over MgSO$_4$, filtered, and solvents removed from the filtrate by rotary evaporation. The resulting residue was chromatographed on silicon gel. The eluate was concentrated by rotary evaporation followed by high vacuum to give 2-phenylpyridine. LC-MS Found: 156.2 (M$^+$+1).

Example 10

A 30 mL of reactor equipped with magnetic stir bar was charged with 16 mg (0.022 mmol) of [(t-Bu)₂P(Cl)PdCl₂]₂, 1.0 (8.8 mmol) of chlorobenzene, 1.3 g (10.66 mmol) of Ph—B(OH)₂, 3.7 g (26.77 mmol) of K₂CO₃ in 5 mL of THF. The reaction mixture was refluxed for 4 hours. The reaction mixture was cooled to room temperature, transferred to a separatory funnel, and diluted with 220 mL of hexane and 150 mL of H₂O. The layers were separated, and organic layer was washed with H₂O (50 mL), brine (100 mL), and dried over MgSO₄, filtered, and solvents removed from the filtrate by rotary evaporation. The resulting residue was chromatographed on silicon gel. The eluate was concentrated by rotary evaporation followed by high vacuum to give 0.72 g (53% yield) of biphenyl.

Example 11

A 30 mL of reactor equipped with magnetic stir bar was charged with 24 mg (0.044 mmol) of (t-Bu)₂PCl)₂PdCl₂,, 1.0 (8.8 mmol) of chlorobenzene, 1.3 g (10.66 mmol) of Ph—B(OH)₂, 3.7 g (26.77 mmol) of K₂CO₃ in 5 mL of THF. The reaction mixture was refluxed for 4 hours. The reaction mixture was cooled to room temperature, transferred to a separatory funnel, and diluted with 220 mL of hexane and 150 mL of H₂O. The layers were separated, and organic layer was washed with H₂O (50 mL), brine (100 mL), and dried over MgSO₄, filtered, and solvents removed from the filtrate by rotary evaporation. The resulting residue was chromatographed on silicon gel. The eluate was concentrated by rotary evaporation followed by high vacuum to give 0.78 g (57% yield) of biphenyl.

Example 12

A 30 mL of reactor equipped with magnetic stir bar was charged with 24 mg (0.044 mmol) of (t-Bu)₂PCl)₂PdCl₂, 1.0 (8.8 mmol) of 2-chloropyridine, 1.3 g (10.66 mmol) of Ph—B(OH)₂, 3.7 g (26.77 mmol) of K₂CO₃ in 5 mL of THF. The reaction mixture was refluxed for 4 hours. The reaction mixture was cooled to room temperature, transferred to a separatory funnel, and diluted with 220 mL of hexane and 150 mL of H₂O. The layers were separated, and organic layer was washed with H₂O (50 mL), brine (100 mL), and dried over MgSO₄, filtered, and solvents removed from the filtrate by rotary evaporation. The resulting residue was chromatographed on silicon gel. The eluate was concentrated by rotary evaporation followed by high vacuum to give 1.3 g (95% yield) of 2-phenylpyridine.

What is claimed is:

1. A process to prepare cross-coupling compounds of the formula R—Q comprising contacting a catalytic amount of a coordination compound having formula (I) with an aryl halide and an arylboronic acid or an arylamine;

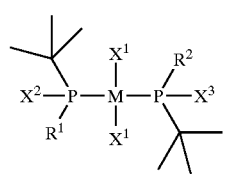

(I)

wherein M is a transition metal;
X¹ is Cl or Br or I; X² is Cl or Br or I; X³ is Cl or Br or I;
and wherein R¹ and R² are independently selected from the group consisting of hydrocarbyl, substituted hydrocarbyl, heterocyclic, organometallic, H, Cl, Br, I, CN, SQ₁, OQ₂, PQ₃Q₄, NQ₅Q₆, SiQ₇Q₈Q₉, and BQ₁₀Q₁₁ where Q₁, Q₂, Q₃, Q₄, Q₅, Q₆, Q₇, Q₈, Q₉, Q₁₀, and Q₁₁ are independently selected from the group consisting of hydrogen, hydrocarbyl substituted hydrocarbyl, hydrocarbylamino, alkoxy, aryloxy, and heterocyclic, and optionally R¹ and R² can together form a ring; and wherein R is optionally an aryl ring;
Q is independently selected from the group consisting of hydrocarbyl, substitute hydrocarbyl, heterocyclic, organometallic, H, CN, SQ1, OQ2, PQ3Q4, NQ5Q6, SiQ7Q8Q9, and BQ10Q11 where Q1, Q2 , Q3, Q4 , Q5 , Q6 , Q7, Q8, Q9, Q10, and Q11 are independently selected from the group consisting of hydrogen, hydrocarbyl substituted hydrocarbyl, hydrocarbylamino, alkoxy, aryloxy, and heterocyclic.

2. A process to prepare cross-coupling compounds of the formula R—Q comprising contacting catalytic amount of a coordination compound having formula (II) with an aryl halide and an arylboronic acid or an arylamine;

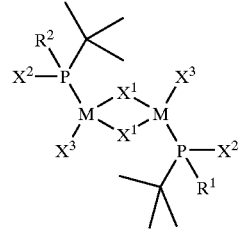

(II)

wherein M is a transition metal;
X1 is Cl or Br or I or O; and X2 is Cl or Br or I; X3 is Cl or Br or I;
R1 and R2 are independently selected from the group consisting of hydrocarbyl, substituted hydrocarbyl, heterocyclic, organometallic, H, Cl, Br, I, CN, SQ1, OQ2, PQ3Q4, NQ5Q6, SiQ7Q8Q9, and BQ10Q11 where Q1, Q2, Q3, Q4, Q5, Q6, Q7, Q8, Q9, Q10, and Q11 are independently selected from the group consisting of hydrogen, hydrocarbyl substituted hydrocarbyl, hydrocarbylamino, alkoxy, aryloxy, and heterocyclic, and optionall R1 and R2 can together form a ring; and wherein R is optionally an aryl ring;
Q is independently selected from the group consisting of hydrocarbyl, substituted hydrocarbyl, heterocyclic, organometallic, H, CN, SQ1, OQ2, PQ3Q4, NQ5Q6, SiQ7Q8Q9, and BQ10Q11 where Q1, Q2, Q3, Q4, Q5, Q6, Q7, Q8, Q9, Q10, and Q11 are independently selected from the group consisting of hydrogen, hydrocarbyl substituted hydrocarbyl, hydrocarbylamino, alkoxy, aryloxy, and heterocyclic.

3. A process to prepare cross-coupling compounds according to claim 1, wherein X1 is Cl, Br, I or O, and R1 and R2 are selected from the group consisting of t-butyl, cyclohexyl, cyclopentyl, i-propyl, ferrocenyl, biphenyl, or phenyl.

4. A process to prepare cross-coupling compounds according to claim 2, wherein R1 and R2 are selected from the group consisting of t-butyl, cyclohexyl, cyclopenty, i-propyl, ferrocenyl, biphenyl, or phenyl.

* * * * *